United States Patent [19]

Schell et al.

[11] Patent Number: 5,075,367

[45] Date of Patent: Dec. 24, 1991

[54] PHENOLIC ANTIOXIDANTS AND STABILIZED ORGANIC COMPOSITIONS

[75] Inventors: Raymond A. Schell, Prairieville, La.; George L. Mina, Orangeburg, S.C.

[73] Assignee: Ethyl Corporation, Richmond, Va.

[21] Appl. No.: 625,370

[22] Filed: Dec. 11, 1990

[51] Int. Cl.$^5$ .......................... C07C 39/06; C08K 5/13
[52] U.S. Cl. ...................................... 524/349; 568/744
[58] Field of Search .......................... 544/744; 524/349

[56] References Cited

U.S. PATENT DOCUMENTS

| | | | |
|---|---|---|---|
| 2,909,504 | 10/1959 | Spacht | 568/744 |
| 4,342,777 | 8/1982 | Jurd | 568/744 |
| 4,612,642 | 9/1986 | Burton | 524/349 |
| 4,870,214 | 9/1989 | Mina et al. | 568/720 |

*Primary Examiner*—Veronica P. Hoke
*Attorney, Agent, or Firm*—Patricia J. Hogan

[57] ABSTRACT

The 2-alkyl-6-t-butyl-4-(pentamethylbenzyl)phenols in which the 2-alkyl group is t-butyl or methyl are novel compounds having melting points sufficiently low to make them attractive as antioxidants for low melting polymers such as polyethylene, polypropylene, and polystyrene.

13 Claims, No Drawings

PHENOLIC ANTIOXIDANTS AND STABILIZED ORGANIC COMPOSITIONS

FIELD OF INVENTION

This invention relates to novel phenols having utility as antioxidants for organic materials.

BACKGROUND

There are many phenols which are known to be effective as antioxidants for organic materials, such as polymers, that are normally susceptible to oxidative deterioration. However, even the phenols which have excellent antioxidant properties are apt to have one or more drawbacks. For example, as mentioned in U.S. Pat. No. 4,870,214 (Mina et al.), 1,3,5-tris(3,5-di-t-butyl-4-hydroxybenzyl)-2,4,6-trimethylbenzene is a superior antioxidant, but it has the disadvantage of having a melting point (240°–245° C.) which is substantially higher than the temperatures at which some polymers, such as polyethylene, some polypropylenes, and polystyrene, are usually processed. Other phenols have the disadvantage of contributing to color development in the organic materials into which they are incorporated.

SUMMARY OF INVENTION

It has now been discovered that 2-alkyl-6-t-butyl-4-(pentamethylbenzyl)phenols in which the 2-alkyl group is t-butyl or methyl contribute minimal color to organic materials in which they are dispersed and have melting points substantially below that of 1,3,5-tris(3,5-di-t-butyl-4-hydroxybenzyl)-2,4,6-trimethylbenzene, thus making them especially attractive for use as antioxidants in low melting polymers, such as polyethylene, polypropylene, and polystyrene.

DETAILED DESCRIPTION

The novel phenols of the invention can be prepared by reacting the appropriate 2-alkyl-6-t-butyl-4-methoxymethylphenol with pentamethylbenzene in the presence of an acid catalyst, such as sulfuric acid or a sulfonic acid. If desired, an excess of pentamethylbenzene may be used to serve as a solvent or co-solvent for the reaction. However, it is ordinarily preferred to employ the reactants in substantially stoichiometric amounts and to conduct the reaction in an inert solvent, such as methylene chloride. After completion of the reaction, the acid layer is drained off, the product solution is neutralized by washing with aqueous sodium bicarbonate, and the solvent is removed by heating over a steam bath. Then, if desired, the product can be purified by recrystallization from an inert solvent, such as heptane or isooctane.

When used as antioxidants, the phenols may be incorporated into any of a wide range of organic materials that are normally susceptible to oxidative deterioration of the type that occurs during or after processing, such as those taught in Mina et al., the teachings of which are incorporated herein by reference. Such organic materials include, e.g., petroleum products, such as lubricating oils and distillate fuels; synthetic ester lubricants; plasticizers, such as dioctyl phthalate; and thermosetting and thermoplastic polymers, including resinous polymers, rubbery polymers, and mixtures thereof.

The organic materials into which the antioxidants are incorporated in a preferred embodiment of the invention are the polymers of ethylenically-unsaturated monomers, such as ethylene, propylene, other alkenes, styrene, vinyl chloride, vinylidene chloride, vinyl acetate, methyl acrylate, methyl methacrylate, and the like, including homopolymers, copolymers, and interpolymers of more than two monomers. The organic materials of particular interest are the polymers of ethylenically-unsaturated hydrocarbons; and, as already mentioned, the invention is of especial benefit in conferring antioxidant protection on the low melting polymers, such as polyethylene, polypropylene, and polystyrene.

When incorporated into organic materials needing antioxidant protection, the antioxidants of the invention are incorporated by any of the suitable techniques conventionally employed for incorporating phenolic antioxidants into such materials; and they may be used in any effective amount, usually an amount in the range of about 0.005–5%, preferably about 0.01–2%, based on the weight of the organic material. Like conventional phenolic antioxidants, they may be used alone or in combination with a synergist, such as dilauryl or distearyl thiodipropionate, which, when employed, is ordinarily utilized in an amount in the range of about 0.001–5% by weight.

The following examples are given to illustrate the invention and are not intended as limitation thereof.

EXAMPLE I

Part A

Charge a suitable autoclave with 440 mL of methanol, 19.6 g (0.65 mol) of paraformaldehyde, 5.3 g (0.048 mol) of 40% aqueous dimethylamine catalyst, and 103 g (0.5 mol) of 2,6-di-t-butylphenol. Seal the autoclave and, while stirring, heat to 130° C. and maintain that temperature for 190 minutes, at the end of which time GC analysis shows the conversion to 2,6-di-t-butyl-4-methoxymethylphenol to be 95% complete. Transfer the mixture to a distillation flask under nitrogen and remove excess methanol. Cool the residue and dissolve it in 290 g of methylene chloride.

Part B

Charge a suitable reaction vessel with 100 mL of methylene chloride and 29.6 g (0.2 mol) of pentamethylbenzene and stir while concurrently feeding two solutions over a period of one hour and maintaining the temperature at 5° C. with an ice bath—one solution being a 100 g aliquot of the product of Part A (0.116 mol of 2,6-di-t-butyl-4-methoxymethylphenol in methylene chloride) and the other solution being 29.8 g of 84% sulfuric acid. Stir the resulting mixture for 15 minutes.

Part C

Transfer the reaction mixture to a separatory funnel, drain out the lower sulfuric acid phase, and add a solution of 7 g of sodium bicarbonate in 240 g of water to the separated solution of product in methylene chloride. Place the resultant mixture in a distillation flask and distill out the methylene chloride to leave the solid product in the aqueous phase. Add hot heptane to extract the solid product, separate the aqueous phase, and wash the hot heptane solution twice with 200 mL of water. Slowly cool the heptane solution to 5° C., filter off the separated solids, and wash the white precipitate with 40 mL of cold heptane to provide a white solid having a melting point of 143° C. Proton NMR analysis confirms the structure as 2,6-di-t-butyl-4-(pentamethylbenzyl) phenol.

EXAMPLE II

Part A

Prepare three formulation from the following ingredients:

|  | A (Control) | B (Comparative) | C (Invention) |
|---|---|---|---|
| Polypropylene powder | 600.0 g | 600.0 g | 600.0 g |
| Calcium stearate | 0.3 g | 0.3 g | 0.3 g |
| 1,3,5-tris(3,5-di-t-butyl-4-hydroxybenzyl)-2,4,6-trimethylbenzene | — | 0.6 g | — |
| 2,6-di-t-butyl-4-(pentamethylbenzyl)phenol | — | — | 0.6 g |

Part B

Test each of the formulations of Part A for melt flow index and yellowness index by extruding them in a Brabender twin screw extruder at 175°–280°–280° C. and 30 rpm under nitrogen and then making five passes through a Brabender single screw extruder at 260° C. and 30 rpm under air. The test results are shown below.

| Formulation | Extrusion Passes | | | |
|---|---|---|---|---|
|  | TS | ss1 | ss3 | ss5 |
| MFI @ 230° C./2160 g Load | | | | |
| A | 9.60 | 28.53 | 96.45 | — |
| B | 4.32 | 5.89 | 8.33 | 10.77 |
| C | 4.22 | 5.67 | 8.20 | 11.07 |
| Yellowness Index | | | | |
| A | 2.79 | 3.14 | 5.80 | — |
| B | 3.88 | 4.86 | 7.35 | 10.88 |
| C | 5.07 | 4.27 | 6.42 | 7.82 |

No ss5 test results can be obtained for Formulation A because polymer degradation is too severe by the fifth pass to permit a representative sample to be collected.

Part C

Compare the UV stability of Formulations B and C by exposing specimens to UV light for four hours, then spraying them with water in the dark at 60° C. for four hours, and repeating the cycle until failure occurs in the form of cracking when the specimen is bent over a solid object. Formulation B fails after 29–41 hours of UV light exposure (53–77 total hours), while Formulation C does not fail until after 41–52 hours of UV light exposure (77–100 total hours).

The preceding data demonstrate the superiority of the antioxidants of the invention in color and UV protection, as well as showing them to be almost equal to 1,3,5-tris(3,5-di-t-butyl-4-hydroxybenzyl)-2,4,6-trimethyl-benzene in protecting melt flow.

What is claimed is:

1. A 2-alkyl-6-t-butyl-4-(pentamethylbenzyl)phenol wherein the 2-alkyl group is t-butyl or methyl.

2. The phenol of claim 1 wherein the 2-alkyl group is t-butyl.

3. The phenol of claim 1 wherein the 2-alkyl group is methyl.

4. A composition comprising an organic material that is normally susceptible to oxidative deterioration and an effective antioxidant amount of a 2-alkyl-6-t-butyl-4-(pentamethylbenzyl)-phenol wherein the 2-alkyl group is t-butyl or methyl.

5. The composition of claim 4 wherein the antioxidant is 2,6-di-t-butyl-4-(pentamethylbenzyl)phenol.

6. The composition of claim 4 wherein the antioxidant is 2-methyl-6-t-butyl-4-(pentamethylbenzyl)-phenol.

7. The composition of claim 4 wherein the organic material is a polymer of an ethylenically-unsaturated monomer.

8. The composition of claim 7 wherein the polymer is polyethylene.

9. The composition of claim 8 wherein the antioxidant is 2,6-di-t-butyl-4-(pentamethylbenzyl)phenol.

10. The composition of claim 7 wherein the polymer is polypropylene.

11. The composition of claim 10 wherein the antioxidant is 2,6-di-t-butyl-4-(pentamethylbenzyl)phenol.

12. The composition of claim 7 wherein the polymer is polystyrene.

13. The composition of claim 12 wherein the antioxidant is 2,6-di-t-butyl-4-(pentamethylbenzyl)phenol.

* * * * *